US012778934B2

(12) United States Patent
Redmer

(10) Patent No.: US 12,778,934 B2
(45) Date of Patent: Nov. 3, 2026

(54) OPHTHALMIC FORMULATION COMPRISING N-[5-(AMINOSULFONYL)-4-METHYL-1,3-THIAZOL-2-YL]-N-METHYL-2-[4-(2-PYRIDINYL)PHENYL]ACETAMIDE HEMIHYDRATE

(71) Applicant: AIC316 GmbH, Wuppertal (DE)

(72) Inventor: Jessica Redmer, Mönchengladbach (DE)

(73) Assignee: AIC316 GmbH, Wuppertal (DE)

( * ) Notice: Subject to any disclaimer, the term of this patent is extended or adjusted under 35 U.S.C. 154(b) by 838 days.

(21) Appl. No.: 17/907,169

(22) PCT Filed: Mar. 25, 2021

(86) PCT No.: PCT/EP2021/057655
§ 371 (c)(1),
(2) Date: Sep. 23, 2022

(87) PCT Pub. No.: WO2021/191320
PCT Pub. Date: Sep. 30, 2021

(65) Prior Publication Data

US 2023/0124969 A1 Apr. 20, 2023

Related U.S. Application Data

(60) Provisional application No. 63/100,693, filed on Mar. 26, 2020.

(30) Foreign Application Priority Data

Jun. 17, 2020 (EP) ..................................... 20180465

(51) Int. Cl.
*A61K 31/426* (2006.01)
*A61K 9/00* (2006.01)
*A61K 47/10* (2017.01)
*A61K 47/38* (2006.01)

(52) U.S. Cl.
CPC .......... *A61K 31/426* (2013.01); *A61K 9/0048* (2013.01); *A61K 47/10* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 11,814,408 B2 | 11/2023 | Cavanagh et al. |
| 2004/0235917 A1 | 11/2004 | Betz et al. |
| 2021/0300963 A1 | 9/2021 | Cavanagh et al. |

FOREIGN PATENT DOCUMENTS

| | | |
|---|---|---|
| KR | 102129426 B1 | 7/2020 |
| WO | WO 2018/095576 | 5/2018 |
| WO | WO 2018/096170 | 5/2018 |

OTHER PUBLICATIONS

Remington Essentials of Pharmaceutics, Chapter 25 Sterilization Processes and Sterility Assurance by Agalloco et al. (Ed. Linda Felton) (Year: 2012).*
Remington Essentials of Pharmaceutics, Chapter 28 Ophthalmic Preparations by Chowhan et al. (Ed. Linda Felton) (Year: 2012).*
Garcia-Valldecabres, et al., Optometry, 75, 160-168) (Year: 2004).*
International Search Report and Written Opinion dated Jun. 24, 2021 for PCT Application No. PCT/EP2021/057655, filed Jun. 24, 2021.

* cited by examiner

*Primary Examiner* — George W Kosturko
*Assistant Examiner* — Jason M. Nolan
(74) *Attorney, Agent, or Firm* — Millen, White, Zelano & Branigan, PC; Brion P. Heaney

(57) ABSTRACT

The present application relates to an ophthalmic formulation that can include N-[5-(aminosulfonyl)-4-methyl-1,3-thiazol-2-yl]-N-methyl-2-[4-(2-pyridinyl)phenyl]acetamide hemihydrate

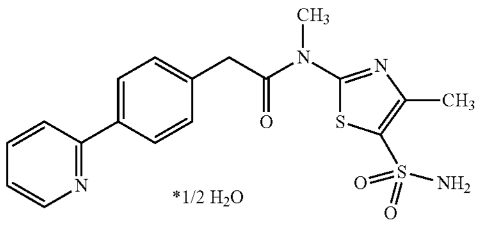

*1/2 $H_2O$ polyethylene glycol, and an artificial tears solution as well as to a method for preparing such an ophthalmic formulation.

17 Claims, No Drawings

OPHTHALMIC FORMULATION COMPRISING N-[5-(AMINOSULFONYL)-4-METHYL-1,3-THIAZOL-2-YL]-N-METHYL-2-[4-(2-PYRIDINYL)PHENYL]ACETAMIDE HEMIHYDRATE

The present application is the national phase entry of PCT Application No. PCT/EP2021/057655, filed Mar. 25, 2021, which claims priority to U.S. Provisional Application No. 63/100,693, filed Mar. 26, 2020 and EP Application No. 20180465.5, filed Jun. 17, 2020, all of which are incorporated by reference in their entireties.

The present invention relates to an ophthalmic formulation comprising N-[5-(aminosulfonyl)-4-methyl-1,3-thiazol-2-yl]-N-methyl-2-[4-(2-pyridinyl)phenyl]acetamide hemihydrate, polyethylene glycol, and an artificial tears solution as well as to a method for preparing such ophthalmic formulation.

BACKGROUND OF THE INVENTION

Synthesis of N-[5-(aminosulfonyl)-4-methyl-1,3-thiazol-2-yl]-N-methyl-2-[4-(2-pyridinyl)phenyl]acetamide is known from WO 01/47904 A1, and the use of acidic components including methanesulfonic acid for the formulation of tablets for the treatment of herpes simplex infections. Such tablets contain micronized N-[5-(aminosulfonyl)-4-methyl-1,3-thiazol-2-yl]-N-methyl-2-[4-(2-pyridinyl)phenyl]acetamide as disclosed by WO 2006/103011 A1.

Applicant's previous invention as disclosed in WO 2018/095576 A1 relates to topical pharmaceutical formulations for the treatment or prevention of herpes virus infections, comprising N-[5-(aminosulfonyl)-4-methyl-1,3-thiazol-2-yl]-N-methyl-2-[4-(2-pyridinyl)phenyl]acetamide. In one embodiment the pharmaceutical formulation is applicable to the eye and in another embodiment the pharmaceutical formulation containing Pritelivir hemihydrate is suitable for the treatment of Herpes keratitis. The topical pharmaceutical formulations of WO 2018/095576 A1 comprise a Pritelivir agent, for instance the hemihydrate of Pritelivir, at least one solvent such as PEG and at least one antioxidant and have a pH value of 2.0 to 8.0, preferably 4.0 to 5.0 and more preferably of 4.0 to 4.5.

Disclosed in WO 2018/095576 A1 is also a formulation as gel containing a gelification agent such as hydroxypropyl methylcellulose (hypromellose). A typical formulation of WO 2018/095576 A1 comprises: 5% by weight of the a Pritelivir agent such as the Pritelivir hemihydrate, 39.1% by weight of SR PEG 400, 9.59% by weight ethanol, 4.8% by weight of a pH-4-buffer, 23.98% by weight of Transcutol HP, 14.39% by weight of dimethyl isosorbide, 1.92% by weight of benzyl alcohol and 1.25% by weight of hydroxypropyl methylcellulose, wherein the pH value of the formulation is in the range of 4.0 to 5.0.

Herpes infections can also occur in the eye and in case the eye herpes only affects the outermost layers of the eye, antiviral eye drops containing an antiviral agent such as Acyclovir can be used for treatment. However, cases of eye herpes are known where the herpes viruses are resistant against the available antiviral herpes agents.

N-[5-(aminosulfonyl)-4-methyl-1,3-thiazol-2-yl]-N-methyl-2-[4-(2-pyridinyl)phenyl]-acetamide is known as an effective antiviral herpes agent which can be administered even in cases where resistance of herpes viruses against other available antiviral herpes agents is observed.

Therefore, it is the objective of the present invention to provide an ophthalmic formulation containing the compound N-[5-(aminosulfonyl)-4-methyl-1,3-thiazol-2-yl]-N-methyl-2-[4-(2-pyridinyl)phenyl]acetamide, so that drug resistant herpes infections of the eye can be treated.

The objective of the present invention is solved by the teachings of the independent claims. Further advantageous features, aspects and details of the invention are evident from the dependent claims, the description, and the examples of the present application.

DESCRIPTION OF THE INVENTION

The present invention is directed to an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution, wherein the artificial tears solution contains glycerin, hypromellose, and polyethylene glycol 400 and optionally povidone.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate.

The compound N-[5-(aminosulfonyl)-4-methyl-1,3-thiazol-2-yl]-N-methyl-2-[4-(2-pyridinyl)phenyl]acetamide is also known under the international nonproprietory name (INN) Pritelivir.

The compound N-[5-(aminosulfonyl)-4-methyl-1,3-thiazol-2-yl]-N-methyl-2-[4-(2-pyridinyl)phenyl]acetamide hemihydrate is also named herein "Pritelivir free base hemihydrate" or just "Pritelivir hemihydrate". The term "free base" in the designation "Pritelivir free base hemihydrate" shall indicate that use of the free base is essential to the invention and that no salts of the compound Pritelivir shall be used under the conditions disclosed herein for the preparation of the ophthalmic formulation.

Pritelivir free base hemihydrate has the following chemical structure:

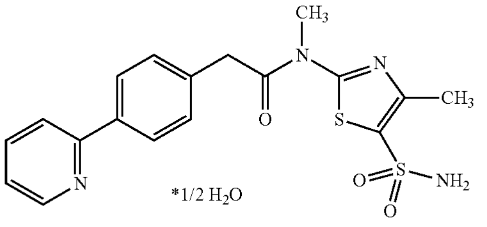 [SMILES: Cc1nc(N(C)C(=O)Cc2ccc(-c3ccccn3)cc2)sc1S(N)(=O)=O]

Several salts of Pritelivir such as the mesylate salt or the maleate salt of Pritelivir are known. However, in the course of developing the herein-described new ophthalmic formulation containing Pritelivir it was surprisingly found that no ophthalmic formulation could be provided on the basis of the tested salts of Pritelivir under the experimental conditions which were suited to provide the herein-described ophthalmic formulation containing Pritelivir free base hemihydrate as drug substance (DS).

Moreover, the observations made in the course of the development of the herein-described new ophthalmic formulation suggest that a salt formation of Pritelivir should be avoided during the preparation of the ophthalmic formulation. Consequently, the present application is directed to an ophthalmic formulation which is free from Pritelivir salts and which is useful for treatment of herpes infections of the eye and especially such herpes infections of the eye which already developed resistance against common antiviral herpes drugs.

PEG: Polyethylene Glycol

One essential component of the ophthalmic formulation of the present application is polyethylene glycol, abbreviated as PEG.

In compatibility studies and solubility studies a larger number of solvents and ingredients had been investigated but unexpectedly only PEG was found to be suitable and acceptable for an ophthalmic formulation of Pritelivir free base hemihydrate.

Polyethylene glycol has the following chemical structure

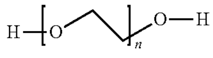

wherein n indicates the number of repeating units.

The chemical formula is $C_{2n}H_{4n+2}O_{n+1}$ and the density is 1.125 g/mL.

Other IUPAC names of PEG are poly(oxyethylene) or poly(ethylene oxide). PEG is also known under the trademarks Carbowax™, Kollisolv®, Kolliphor®, Polyglycol™ and the Ph. Eur. (Pharmacopoea Europaea) name Macrogol.

Several different polyethylene glycols such as PEG 200, PEG 300, PEG 400, PEG 600, PEG 1000, PEG 1500, PEG 2000, PEG 3000, PEG 4000, PEG 6000, PEG 8000 and so on are known.

The numbers in the names of the PEGs indicate their average molecular weight, e.g. a PEG with n=9 has an average molecular weight of approximately 400 daltons, and is usually designated as PEG 400. Most PEGs include molecules with a distribution of molecular weights, i.e. they are polydisperse.

The size distribution can be characterized statistically by its weight average molecular weight (Mw) and its number average molecular weight (Mn), the ratio of which is called the polydispersity index (Mw/Mn). Mw and Mn can be measured by mass spectrometry.

It was found that polyethylene glycols having an average molecular weight in the range of from 200 g/mol to 400 g/mol are suitable for the present ophthalmic formulation. The use of PEG 400 is particularly preferred for the present ophthalmic formulation.

However, it is also possible to use mixtures of PEGs for the ophthalmic formulation. PEGs having an average molecular weight in the range of from 200 g/mol to 400 g/mol are at room temperature non-volatile liquids.

The terms "in the range of from 'value A' to 'value B'" and "an amount of from 'value A' to 'value B'" as used throughout the present application refers to a continuous group of possible values, wherein 'value A' represents the lower end of said group and 'value B' represents the upper end of said group. Values representing said lower and said upper ends are included in said group of possible values. For example, PEGs having an average molecular weight in the range of from 200 g/mol to 400 g/mol include PEGs having an average molecular weight of 200 g/mol and PEGs having an average molecular weight of 400 g/mol as well as PEGs having average molecular weights which are in between.

The term "room temperature" as used herein, is synonymous to the term "standard room temperature" and refers to a temperature in the range of from 19° C. to 26° C. For example, PEGs which are "at room temperature non-volatile liquids" means that said PEGs are non-volatile liquids "at a temperature in the range of from 19° C. to 26° C.".

Therefore, it is also in accordance with the present invention to use mixtures of two, three or more PEGs in the ophthalmic formulation. For instance, mixtures of PEG 300 and PEG 400, or PEG 200 and PEG 400, or PEG 200 and PEG 300 and PEG 400, and so on.

The average molecular weight of all mixtures of PEGs used for the present ophthalmic formulation should be in the range of from 200 g/mol to 400 g/mol, preferably in the range of from 300 g/mol to 400 g/mol, and more preferably in the range of from 350 g/mol to 400 g/mol, and most preferably around 400 g/mol.

Therefore, the present application is also directed to an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200, PEG 300, PEG 400, or a mixture of two or more of these PEGs, and
c) artificial tears solution, wherein the artificial tears solution contains glycerin, hypromellose, and polyethylene glycol 400 and optionally povidone.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) PEG 200, PEG 300, PEG 400, or a mixture of two or more of these PEGs, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200, PEG 300, PEG 400, or a mixture of two or more of these PEGs, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate.

Preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200 and/or PEG 400, preferably PEG 400, and
c) artificial tears solution, wherein the artificial tears solution contains glycerin, hypromellose, and polyethylene glycol 400 and optionally povidone.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate.

The PEG or the mixture of PEGs used in the present ophthalmic formulation is responsible for the solubility of Pritelivir free base hemihydrate, i.e. without the PEG or the mixture of PEGs the desired amount of Pritelivir free base hemihydrate cannot be dissolved in the ophthalmic formulation and precipitation occurs, reducing the amount of effective drug substance (i.e. Pritelivir free base hemihydrate) in the ophthalmic formulation so that no ophthalmic formulation with a defined amount of effective drug substance can be prepared.

Moreover, the PEG or the mixture of PEGs used in the present ophthalmic formulation is responsible for the viscosity of the ophthalmic formulation. Therefore, it is preferred that the PEG or the mixture of PEGs is selected such that the viscosity of the ophthalmic formulation is in the range of from 25 cps to 50 cps.

In addition to the PEG or the mixture of PEGs used for the present ophthalmic formulation also the selection of the artificial tears solution has an impact on the viscosity of the ophthalmic formulation. Taking into consideration that the artificial tears solution is normally the main component of the ophthalmic formulation, the viscosity of the ophthalmic formulation of the present application is essentially the same as the viscosity of the artificial tears solution. However, the PEG or the mixture of PEGs present in the ophthalmic formulation can change the viscosity of the artificial tears solution so that the ophthalmic formulation has preferably a viscosity which is identical or up to 20% different from that of the artificial tears solution.

This means that, if the artificial tears solution has for example a viscosity of 40 cps, the ophthalmic formulation of the present application has preferably a viscosity in the range of from 32 cps to 48 cps, and has more preferably a viscosity close to 40 cps.

In general, the ophthalmic formulation of the present invention should have a viscosity in the range of from 10 cps to 100 cps, preferably in the range of from 15 cps to 80 cps, more preferably in the range of from 20 cps to 60 cps, still more preferably in the range of from 25 cps to 50 cps, and still more preferably in the range of from 30 cps to 40 cps.

Many everyday fluids have viscosities between 0.5 and 1000 cP. For instance, water has a viscosity of 1 cp. The lacrimal fluid has a viscosity in the range of from 1.0 cp to 6.0. Ophthalmic formulations with a viscosity up to 20 cp are well tolerated. However, in order to ensure that the ophthalmic formulation remains sufficiently long in the eye, viscosities between 25 cp and 50 cp are preferred and result normally only in an increased reflex regarding the tearing and blinking of the treated eye.

The viscosity of a solution is given in poise units. The poise is the unit of the dynamic viscosity (i.e., the absolute viscosity). The unit centipoise (cp or the plural cps) is equal to 0.01 poise. The SI unit of the viscosity is Pascal-second (Pa*s), equivalent to Newton-second per square meter ($N*s*m^{-2}$).

$$1000\ cp=10\ p=1\ Pa*s=1\ N*s*m^{-2}=1\ kg*m*^{-1}*s^{-1}$$

Thus, in order to obtain the desired viscosity, it is also possible to add a viscosity enhancer to the inventive ophthalmic formulation.

Suitable viscosity enhancers are hydroxyethylcellulose, polyvinyl alcohol, hydroxypropylmethylcellulose, methylcellulose, and polyvinylpyrrolidone. The viscosity enhancer should not be used in the ophthalmic formulation in an amount exceeding 1.0 weight %.

Therefore, the present application is also directed to an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution containing glycerin, hypromellose, and polyethylene glycol 400 and optionally povidone, wherein the ophthalmic formulation has a viscosity in the range of from 25 cp to 50 cp.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a viscosity in the range of from 25 cp to 50 cp.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a viscosity in the range of from 25 cp to 50 cp.

Preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200, PEG 300, PEG 400, or a mixture of two or more of these PEGs, and
c) artificial tears solution containing glycerin, hypromellose, and polyethylene glycol 400 and optionally povidone, wherein the ophthalmic formulation has a viscosity in the range of from 25 cp to 50 cp.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) PEG 200, PEG 300, PEG 400, or a mixture of two or more of these PEGs, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a viscosity in the range of from 25 cp to 50 cp.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200, PEG 300, PEG 400, or a mixture of two or more of these PEGs, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a viscosity in the range of from 25 cp to 50 cp.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200 and/or PEG 400, preferably PEG 400, and
c) artificial tears solution containing glycerin, hypromellose, and polyethylene glycol 400 and optionally povidone, wherein the ophthalmic formulation has a viscosity in the range of from 25 cp to 50 cp.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a viscosity in the range of from 25 cp to 50 cp.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a viscosity in the range of from 25 cp to 50 cp.

The pH value of the ophthalmic formulation of the present application should be in the range of from 4.0 to 8.5, preferably in the range of from 4.2 to 8.0, more preferably in the range of from 4.5 to 7.5, still more preferably in the range of from 5.0 to 7.0, still more preferably in the range of from 5.5 to 6.5, and still more preferably in the range of from 5.7 to 6.3.

Although the lacrimal fluid has a physiological pH value of about 7.4, the experiments revealed herein demonstrated that pH values below 7.0 are beneficial over pH values above pH 7.0.

Preferably, the pH value of the ophthalmic formulation is adjusted by the addition of aqueous hydrochlorid acid solution, preferably by the addition of a 0.1M $HCl_{aq}$ solution.

For pH adjustment hydrochloric acid or hydrobromic acid are preferred and especially preferred is hydrochloric acid.

The use of acidic solutions of acids which tend to form salts, especially hardly soluble or insoluble salts should be avoided. The acids which should be avoided are, for instance, sulfuric acid, phosphoric acid, acetic acid, citric acid, oxalic acid, malonic acid, salicylic acid, p-aminosalicylic acid, malic acid, fumaric acid, succinic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, D-o-tolyltartaric acid, tartronic acid, (o, m, p)-toluic acid, naphthylamine sulfonic acid, trifluoroacetic acid.

Therefore, the present application is also directed to an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution containing glycerin, hypromellose, and polyethylene glycol 400 and optionally povidone, wherein the ophthalmic formulation has a pH value in the range of from 5.0 to 7.0, preferably in the range of from 5.5 to 6.5.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a pH value in the range of from 5.0 to 7.0, preferably in the range of from 5.5 to 6.5.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a pH value in the range of from 5.0 to 7.0, preferably in the range of from 5.5 to 6.5.

Preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200, PEG 300, PEG 400, or a mixture of two or more of these PEGs, and
c) artificial tears solution containing glycerin, hypromellose, and polyethylene glycol 400 and optionally povidone, wherein the ophthalmic formulation has a pH value in the range of from 5.0 to 7.0, preferably in the range of from 5.5 to 6.5.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) PEG 200, PEG 300, PEG 400, or a mixture of two or more of these PEGs, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a pH value in the range of from 5.0 to 7.0, preferably in the range of from 5.5 to 6.5.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200, PEG 300, PEG 400, or a mixture of two or more of these PEGs, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a pH value in the range of from 5.0 to 7.0, preferably in the range of from 5.5 to 6.5.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200 and/or PEG 400, preferably PEG 400, and
c) artificial tears solution containing glycerin, hypromellose, and polyethylene glycol 400 and optionally povidone, wherein the ophthalmic formulation has a pH value in the range of from 5.0 to 7.0, preferably in the range of from 5.5 to 6.5.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a pH value in the range of from 5.0 to 7.0, preferably in the range of from 5.5 to 6.5.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a pH value in the range of from 5.0 to 7.0, preferably in the range of from 5.5 to 6.5.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution containing glycerin, hypromellose, and polyethylene glycol 400 and optionally povidone, wherein the ophthalmic formulation has a viscosity in the range of from 25 cp to 50 cp and a pH value in the range of from 5.0 to 7.0, preferably in the range of from 5.5 to 6.5.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a viscosity in the range of from 25 cp to 50 cp and a pH value in the range of from 5.0 to 7.0, preferably in the range of from 5.5 to 6.5.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the ophthalmic formulation has a viscosity in the range of from 25 cp to 50 cp and a pH value in the range of from 5.0 to 7.0, preferably in the range of from 5.5 to 6.5.

Artificial Tears Solution

Artificial tears solutions also known as tears replacement solutions are used to dilute or replace lacrimal fluid so that artificial tears solutions are used in ophthalmic formulations due to their eye compatibility.

Artificial tears solutions which could be used for the ophthalmic formulation of the present application are, for instance, Thera® Tears solution, GenTeal® Tears solution, Visine® Tears solution, Lac-Ophtal MP, Protagent®, Vidisept® EDO, WET-Comod®, Berberil® Dry Eye, Berberil® Dry Eye EDO, Artelac®, Yxin Teras®, Hylo-Comod®, Hyabak®, Artelac® splash MDO/EDO, Vislube®, Bepanthen eye drops (+dexpanthenol), Opticalm eye drops (+hypromellose), and others.

The artificial tears solution can be purchased as ready-to-use solution or can be prepared from commonly used and well available substances.

Common ingredients of an artificial tears solution are glycerin, hypromellose, and polyethylene glycol as lubricant and in addition normally 10 to all of the following substances are contained: carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and/or sodium lactate. All these substances are dissolved in purified water.

In accordance with the experiments performed and disclosed herein, the Visine® Tears solution or an equivalent artificial tears solution is the preferred artificial tears solution for the ophthalmic formulation.

The Visine® Tears solution contains 0.2% by weight glycerin, 0.2% by weight hypromellose, and 1% by weight PEG 400. In addition to these lubricants, the following substances are present in Visine® Tears solution: carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate. An artificial tears solution which is equivalent to the Visine® Tears solution contains substantially the same ingredients. However, it might lack one or more of the afore-mentioned ingredients or additionally contain one or more pharmaceutically acceptable ingredients as long as it exhibits substantially the same properties of the Visine® Tears solution. An artificial tears solution which is equivalent to the Visine® Tears solution may also contain some or all of the afore-mentioned ingredients in different amounts as long as it exhibits substantially the same properties of the Visine® Tears solution. The term "substantially the same properties" as used in the present application refers to the physicochemical characteristics of a particular formulation which is acceptable for use as an artificial tears solution. For example, an artificial tears solution which has substantially the same properties as the Visine® Tears solution has a pH which differs not more than 5% from the pH of a Visine® Tears solution and/or a viscosity which differs not more than 5% from the viscosity of a Visine® Tears solution and/or a density which differs not more than 10% of from the density of a Visine® Tears solution.

Also disclosed herein is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution.

Also disclosed herein is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200, PEG 300, PEG 400, or a mixture of two or more of these PEGs, and
c) artificial tears solution.

Also disclosed herein is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200 and/or PEG 400, preferably PEG 400, and
c) artificial tears solution.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) Visine® Tears solution.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200, PEG 300, PEG 400, or a mixture of two or more of these PEGs, and
c) Visine® Tears solution.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200 and/or PEG 400, preferably PEG 400, and
c) Visine® Tears solution.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) Visine® Tears solution, wherein the ophthalmic formulation has a pH value in the range of from 5.0 to 7.0, preferably in the range of from 5.5 to 6.5.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200, PEG 300, PEG 400, or a mixture of two or more of these PEGs, and
c) Visine® Tears solution, wherein the ophthalmic formulation has a pH value in the range of from 5.0 to 7.0, preferably in the range of from 5.5 to 6.5.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200 and/or PEG 400, preferably PEG 400, and
c) Visine® Tears solution, wherein the ophthalmic formulation has a pH value in the range of from 5.0 to 7.0, preferably in the range of from 5.5 to 6.5.

Concerning the present ophthalmic formulation it is preferred that the polyethylene glycol is contained in the ophthalmic formulation in an amount of from 20 μg per ml ophthalmic formulation to 100 μg per ml ophthalmic formulation, more preferably in an amount of from 30 μg per ml ophthalmic formulation to 90 μg per ml ophthalmic formulation, more preferably in an amount of from 35 μg per ml ophthalmic formulation to 80 μg per ml ophthalmic formulation, more preferably in an amount of from 40 μg per ml ophthalmic formulation to 70 μg per ml ophthalmic formulation, still more preferably in an amount of from 45 μg per ml ophthalmic formulation to 65 μg per ml ophthalmic formulation, still more preferably in an amount of from 50 μg per ml ophthalmic formulation to 60 μg per ml ophthalmic formulation.

Therefore, the present application is also directed to an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution containing glycerin, hypromellose, and polyethylene glycol 400 and optionally povidone, wherein the polyethylene glycol is contained in the ophthalmic formulation in an amount of from 40 μg per ml ophthalmic formulation to 70 μg per ml ophthalmic formulation.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation.

All embodiments of ophthalmic formulations according to the invention as disclosed herein contain glycerin, hypromellose (also named hydroxypropyl methylcellulose), polyethylene glycol 400, and water as solvent and preferably one, more preferably two, more preferably three, more preferably four, still more preferably five, still more preferably six, still more preferably seven, still more preferably eight, still more preferably nine, still more preferably ten, still more preferably eleven, still more preferably twelve, still more preferably thirteen, still more preferably fourteen, still more preferably fifteen, still more preferably sixteen, still more preferably seventeen or most preferably all eighteen compounds selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200, PEG 300, PEG 400, or a mixture of two or more of these PEGs, and
c) artificial tears solution containing glycerin, hypromellose, and polyethylene glycol 400 and optionally povidone, wherein the polyethylene glycol is contained in the ophthalmic formulation in an amount of from 40 μg per ml ophthalmic formulation to 70 μg per ml ophthalmic formulation.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) PEG 200, PEG 300, PEG 400, or a mixture of two or more of these PEGs, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200, PEG 300, PEG 400, or a mixture of two or more of these PEGs, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200 and/or PEG 400, preferably PEG 400, and
c) artificial tears solution containing glycerin, hypromellose, and polyethylene glycol 400 and optionally povidone, wherein the polyethylene glycol is contained in the ophthalmic formulation in an amount of from 40 μg per ml ophthalmic formulation to 70 μg per ml ophthalmic formulation.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 µg per ml ophthalmic formulation to 70 µg per ml ophthalmic formulation.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate, b) polyethylene glycol, and c) Visine® Tears solution, wherein the polyethylene glycol is contained in the ophthalmic formulation in an amount of from 40 µg per ml ophthalmic formulation to 70 µg per ml ophthalmic formulation.

In all embodiments disclosed herein the amount of polyethylene glycol if explicitly stated like in the ten embodiments disclosed above refers to the total amount of polyethylene glycol present in the formulation which is the cumulative amount of the polyethylene glycol of step b) and step c). Although if different polyethylene glycols are used in step b) and step c) like PEG 200 in step b) and PEG 400 in step c), the stated amount of polyethylene glycol refers to the amount of the PEG of step b) plus the amount of PEG of step c).

Concerning the present ophthalmic formulation it is preferred that the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 20 µg per ml ophthalmic formulation to 100 µg per ml ophthalmic formulation, more preferably in an amount of from 25 µg per ml ophthalmic formulation to 90 µg per ml ophthalmic formulation, more preferably in an amount of from 30 µg per ml ophthalmic formulation to 80 µg per ml ophthalmic formulation, more preferably in an amount of from 35 µg per ml ophthalmic formulation to 70 µg per ml ophthalmic formulation, still more preferably in an amount of from 40 µg per ml ophthalmic formulation to 60 µg per ml ophthalmic formulation, still more preferably in an amount of from 45 µg per ml ophthalmic formulation to 55 µg per ml ophthalmic formulation.

Therefore, the present application is also directed to an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate, b) polyethylene glycol, and c) artificial tears solution containing glycerin, hypromellose, and polyethylene glycol 400 and optionally povidone, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 µg per ml ophthalmic formulation to 60 µg per ml ophthalmic formulation.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and b) polyethylene glycol, and c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 µg per ml ophthalmic formulation to 60 µg per ml ophthalmic formulation.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and b) polyethylene glycol, and c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 µg per ml ophthalmic formulation to 60 µg per ml ophthalmic formulation.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate, b) PEG 200, PEG 300, PEG 400, or a mixture of two or more of these PEGs, and c) artificial tears solution containing glycerin, hypromellose, and polyethylene glycol 400 and optionally povidone, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 µg per ml ophthalmic formulation to 60 µg per ml ophthalmic formulation.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and b) PEG 200, PEG 300, PEG 400, or a mixture of two or more of these PEGs, and c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 µg per ml ophthalmic formulation to 60 µg per ml ophthalmic formulation.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200, PEG 300, PEG 400, or a mixture of two or more of these PEGs, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

Also preferred is an ophthalmic formulation comprising or consisting of:
a) N-[5-(aminosulfonyl)-4-methyl-1,3-thiazol-2-yl]-N-methyl-2-[4-(2-pyridinyl)phenyl]acetamide hemihydrate,
b) PEG 200 and/or PEG 400, preferably PEG 400, and
c) artificial tears solution containing glycerin, hypromellose, and polyethylene glycol 400 and optionally povidone, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

The present invention is also directed to an ophthalmic formulation comprising:
a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

The present invention is also directed to an ophthalmic formulation consisting of:
a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

Also preferred is an ophthalmic formulation comprising or consisting of:
a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) Visine® Tears solution, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

Also preferred is an ophthalmic formulation comprising or consisting of:
a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution containing glycerin, hypromellose, and polyethylene glycol 400 and optionally povidone, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

The present invention is also directed to an ophthalmic formulation comprising:
a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

The present invention is also directed to an ophthalmic formulation consisting of:
a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200, PEG 300, PEG 400, or a mixture of two or more of these PEGs, and
c) artificial tears solution containing glycerin, hypromellose, and polyethylene glycol 400 and optionally povidone, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) PEG 200, PEG 300, PEG 400, or a mixture of two or more of these PEGs, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200, PEG 300, PEG 400, or a mixture of two or more of these PEGs, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) PEG 200 and/or PEG 400, preferably PEG 400, and
c) artificial tears solution containing glycerin, hypromellose, and polyethylene glycol 400 and optionally povidone, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate, b) polyethylene glycol, and c) Visine® Tears solution, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate, b) polyethylene glycol, and c) artificial tears solution containing glycerin, hypromellose, and polyethylene glycol 400 and optionally povidone, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and b) polyethylene glycol, and c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and b) polyethylene glycol, and c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate, b) PEG 200, PEG 300, PEG 400, or a mixture of two or more of these PEGs, and c) artificial tears solution containing glycerin, hypromellose, and polyethylene glycol 400 and optionally povidone, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and b) PEG 200, PEG 300, PEG 400, or a mixture of two or more of these PEGs, and c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and b) PEG 200, PEG 300, PEG 400, or a mixture of two or more of these PEGs, and c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate, b) PEG 200 and/or PEG 400, preferably PEG 400, and c) artificial tears solution containing glycerin, hypromellose, and polyethylene glycol 400 and optionally povidone, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and b) PEG 200 and/or PEG 400, preferably PEG 400, and c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and b) PEG 200 and/or PEG 400, preferably PEG 400, and c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate, b) polyethylene glycol, and c) Visine® Tears solution, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate, b) polyethylene glycol, and c) artificial tears solution containing glycerin, hypromellose, and polyethylene glycol 400 and optionally povidone, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and b) polyethylene glycol, and c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and b) polyethylene glycol, and c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate, b) PEG 200, PEG 300, PEG 400, or a mixture of two or more of these PEGs, and c) artificial tears solution containing glycerin, hypromellose, and polyethylene glycol 400 and optionally povidone, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and b) PEG 200, PEG 300, PEG 400, or a mixture of two or more of these PEGs, and c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and b) PEG 200, PEG 300, PEG 400, or a mixture of two or more of these PEGs, and c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate, b) PEG 200 and/or PEG 400, preferably PEG 400, and c) artificial tears solution containing glycerin, hypromellose, and polyethylene glycol 400 and optionally povidone, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) PEG 200 and/or PEG 400, preferably PEG 400, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

Also preferred is an ophthalmic formulation comprising or consisting of:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) Visine® Tears solution, wherein the polyethylene glycol is contained in the ophthalmic formulation in an amount of from 40 μg per ml ophthalmic formulation to 70 μg per ml ophthalmic formulation and the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount of from 40 μg per ml ophthalmic formulation to 60 μg per ml ophthalmic formulation and the ophthalmic formulation has a pH value in the range of from 5.0 to 7.0, preferably in the range of from 5.5 to 6.5.

Concerning the present ophthalmic formulation it is preferred that the artificial tears solution is contained in the ophthalmic formulation in an amount of from 0.5 g per ml ophthalmic formulation to 1.7 g per ml ophthalmic formulation, more preferably in an amount of from 0.6 g per ml ophthalmic formulation to 1.6 g per ml ophthalmic formulation, more preferably in an amount of from 0.7 g per ml ophthalmic formulation to 1.5 g per ml ophthalmic formulation, still more preferably in an amount of from 0.8 g per ml ophthalmic formulation to 1.4 g per ml ophthalmic formulation, still more preferably in an amount of from 0.9 g per ml ophthalmic formulation to 1.3 g per ml ophthalmic formulation, still more preferably in an amount of from 1.0 g per ml ophthalmic formulation to 1.2 g per ml ophthalmic formulation.

The ophthalmic formulation of the present application is used for prophylaxis and/or treatment of diseases, caused by herpes simplex viruses, and/or prevention of transmission of a herpes virus or herpes viruses.

Preferably, the ophthalmic formulation of the present application is used for prophylaxis and/or treatment of herpes simplex infections of the eye, especially of ocular herpes (i.e. keratitis).

Thus, in some preferred embodiments, the present application is directed to an ophthalimic formulation comprising:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution containing glycerin, hypromellose, and polyethylene glycol 400 and optionally povidone, for use in the prophylaxis and/or treatment of diseases caused by herpes simplex viruses, and/or prevention of transmission of a herpes virus or herpes viruses. The diseases caused by herpes simplex viruses are preferably herpes simplex infections of the eye, especially of ocular herpes (i.e. keratitis).

The present invention is also directed to an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, for use in the prophylaxis and/or treatment of diseases caused by herpes simplex viruses, and/or prevention of transmission of a herpes virus or herpes viruses. The diseases caused by herpes simplex viruses are preferably herpes simplex infections of the eye, especially of ocular herpes (i.e. keratitis).

The present invention is also directed to an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, for use in the prophylaxis and/or treatment of diseases caused by herpes simplex viruses, and/or prevention of transmission of a herpes virus or herpes viruses. The diseases caused by herpes simplex viruses are preferably herpes simplex infections of the eye, especially of ocular herpes (i.e. keratitis).

Consequently, an aspect of the present application is the use of N-[5-(aminosulfonyl)-4-methyl-1,3-thiazol-2-yl]-N-methyl-2-[4-(2-pyridinyl)phenyl]acetamide hemihydrate in the prophylaxis and/or treatment of diseases caused by herpes simplex viruses, and/or in the prevention of transmission of a herpes virus or herpes viruses. The N-[5-(aminosulfonyl)-4-methyl-1,3-thiazol-2-yl]-N-methyl-2-[4-(2-pyridinyl)phenyl]acetamide hemihydrate is preferably administered as ophthalimic formulation as disclosed herein. Preferred is an administration of one to five drops of an ophthalimic formulation as disclosed herein two or three times a day.

As used herein the term "prevent", "preventing", "prevention" or "prophylaxis" means no disorder or disease development if none had occurred, or no further disorder or disease development if there had already been development of the disorder or disease. Also considered is the ability of one to prevent some or all of the symptoms associated with the disorder or disease. Prevention of diseases means prophylaxis of diseases and prophylaxis of diseases means prevention of diseases. Thus, the terms "prophylaxis" and "prevention" are used interchangeably throughout the present application.

The ophthalmic formulation of the present application can also be used together or in combination with a further antiviral agent such as an antimetabolite and preferably a nucleobase analogue, nucleotide analogues or nucleoside analogue drug. It is further preferred if the further antiviral agent is useful against herpes viruses and/or against transmission of a herpes virus or herpes viruses and is selected from the group of drugs comprising but not limited to or consisting of: acetylsalicylic acid, trifluridine, idoxuridine, foscarnet, cidofovir, ganciclovir, acyclovir, penciclovir, or the respective prodrugs valaciclovir, valganciclovir, or famciclovir.

Another aspect of the present invention is directed to a method of prophylaxis or treatment of diseases caused by herpes simplex viruses, and/or prevention of transmission of a herpes virus or herpes viruses comprising:

administering an effective amount of the ophthalmic formulation of the present invention comprising
a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution containing glycerin, hypromellose, and polyethylene glycol 400 and optionally povidone, to a patient in need of such treatment. Preferably the diseases caused by herpes simplex virus are herpes simplex infections of the eye, especially of ocular herpes (i.e. keratitis).

Another aspect of the present invention is directed to a method of prophylaxis or treatment of diseases caused by herpes simplex viruses, and/or prevention of transmission of a herpes virus or herpes viruses comprising:

administering an effective amount of the ophthalmic formulation of the present invention comprising
a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, to a patient in need of such treatment. Preferably the diseases caused by herpes simplex virus are herpes simplex infections of the eye, especially of ocular herpes (i.e. keratitis).

Another aspect of the present invention is directed to a method of prophylaxis or treatment of diseases caused by herpes simplex viruses, and/or prevention of transmission of a herpes virus or herpes viruses comprising:

administering an effective amount of the ophthalmic formulation of the present invention consisting of
a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, to a patient in need of such treatment. Preferably the diseases caused by herpes simplex virus are herpes simplex infections of the eye, especially of ocular herpes (i.e. keratitis).

Said method can also be used together or in combination with a further antiviral agent such as an antimetabolite and preferably a nucleobase analogue, nucleotide analogues or nucleoside analogue drug. Preferably the further antiviral agent is effective against herpes viruses and/or against transmission of a herpes virus or herpes viruses and is preferably selected from the group of drugs comprising but not limited to or consisting of: acetylsalicylic acid, trifluridine, idoxuridine, foscarnet, cidofovir, ganciclovir, acyclovir, penciclovir, or the respective prodrugs valaciclovir, valganciclovir, or famciclovir.

Thus, an aspect of the present application is a method of prophylaxis or treatment of diseases caused by herpes simplex viruses, and/or prevention of transmission of a herpes virus or herpes viruses comprising administering an effective amount of N-[5-(aminosulfonyl)-4-methyl-1,3-thiazol-2-yl]-N-methyl-2-[4-(2-pyridinyl)phenyl]acetamide hemihydrate to a patient in need thereof. The N-[5-(aminosulfonyl)-4-methyl-1,3-thiazol-2-yl]-N-methyl-2-[4-(2-pyridinyl)phenyl]acetamide hemihydrate is preferably administered as ophthalimic formulation as disclosed herein. Preferred is an administration of one to five drops of an ophthalimic formulation as disclosed herein two or three times a day.

The N-[5-(aminosulfonyl)-4-methyl-1,3-thiazol-2-yl]-N-methyl-2-[4-(2-pyridinyl)phenyl]acetamide hemihydrate can also be administered together with a further antiviral agent such as an antimetabolite and preferably a nucleobase analogue, nucleotide analogues or nucleoside analogue drug. Preferred drugs are acetylsalicylic acid, trifluridine, idoxuridine, foscarnet, cidofovir, ganciclovir, acyclovir, penciclovir, valaciclovir, valganciclovir, or famciclovir. This further drug can be contained in the same ophthalimic formulation or in a further ophthalimic formulation which is administered at the same time or within certain time intervals in relation to administration of the N-[5-(aminosulfonyl)-4-methyl-1,3-thiazol-2-yl]-N-methyl-2-[4-(2-pyridinyl)phenyl]acetamide hemihydrate.

Another aspect of the present invention is directed to the use of N-[5-(amino-sulfonyl)-4-methyl-1,3-thiazol-2-yl]-N-methyl-2-[4-(2-pyridinyl)phenyl]acetamide hemihydrate for the preparation of an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution containing glycerin, hypromellose, and polyethylene glycol 400 and optionally povidone, for the prophylaxis and/or treatment of diseases caused by herpes simplex viruses, and/or prevention of transmission of a herpes virus or herpes viruses. Preferably such diseases caused by herpes simplex viruses are herpes simplex infections of the eye, especially of ocular herpes (i.e. keratitis).

Another aspect of the present invention is directed to the use of N-[5-(amino-sulfonyl)-4-methyl-1,3-thiazol-2-yl]-N-methyl-2-[4-(2-pyridinyl)phenyl]acetamide hemihydrate for the preparation of an ophthalmic formulation comprising:

a) N-[5-(aminosulfonyl)-4-methyl-1,3-thiazol-2-yl]-N-methyl-2-[4-(2-pyridinyl)phenyl]acetamide hemihydrate,
b) polyethylene glycol, and
c) artificial tears solution containing glycerin, hypromellose, polyethylene glycol 400, carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, for the prophylaxis and/or treatment of diseases caused by herpes simplex viruses, and/or prevention of transmission of a herpes virus or herpes viruses.

Preferably such diseases caused by herpes simplex viruses are herpes simplex infections of the eye, especially of ocular herpes (i.e. keratitis).

Another aspect of the present invention is directed to the use of N-[5-(amino-sulfonyl)-4-methyl-1,3-thiazol-2-yl]-N-methyl-2-[4-(2-pyridinyl)phenyl]acetamide hemihydrate for the preparation of an ophthalmic formulation consisting of:

a) N-[5-(aminosulfonyl)-4-methyl-1,3-thiazol-2-yl]-N-methyl-2-[4-(2-pyridinyl)phenyl]acetamide hemihydrate, and
b) polyethylene glycol, and
c) artificial tears solution consisting of glycerin, hypromellose, polyethylene glycol 400, water as solvent, and at least one compound selected from the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate, for the prophylaxis and/or treatment of diseases caused by herpes simplex viruses, and/or prevention of transmission of a herpes virus or herpes viruses. Preferably such diseases caused by herpes simplex viruses are herpes simplex infections of the eye, especially of ocular herpes (i.e. keratitis).

As discussed in the introductory part, Applicant's previous invention as disclosed in WO 2018/095576 A1 could be regarded as closest prior art disclosing topical pharmaceutical formulations for the treatment or prevention of herpes virus infections. These topical formulations may contain N-[5-(aminosulfonyl)-4-methyl-1,3-thiazol-2-yl]-N-methyl-2-[4-(2-pyridinyl)phenyl]acetamide hemihydrate, at least one solvent such as PEG and at least one antioxidant and have a pH value of 2.0 to 8.0, preferably 4.0 to 5.0 and more preferably of 4.0 to 4.5.

However, WO 2018/095576 A1 does not disclose an ophthalmic formulation of N-[5-(aminosulfonyl)-4-methyl-1,3-thiazol-2-yl]-N-methyl-2-[4-(2-pyridinyl)phenyl]acetamide hemihydrate (Pritelivir free base hemihydrate), PEG (polyethylene glycol), and an artificial tears solution containing glycerin, hypromellose, and polyethylene glycol 400 and optionally povidone.

During the development of the ophthalmic formulations disclosed herein it was found that the Pritelivir free base hemihydrate is not stable in most of the artificial tears solutions at pH 4.0 and precipitates. Even worse it was found that the precipitation increases with increasing pH value. Consequently, the objective of the present invention was to invent an artificial tears solution of a Pritelivir agent, wherein the Pritelivir agent is stable at a pH value of 6.0 to 7.0 which is the optimal and required pH range for eye applications.

Surprisingly, it was found that the Pritelivir hemihydrate as Pritelivir agent is sufficiently stable for an ophthalmic formulation at a pH value between 6.0 and 7.0 if the ophthalmic formulation contains glycerin, hypromellose, and polyethylene glycol 400. Such an ophthalmic formulation is neither disclosed in nor suggested by the state of the art including WO 2018/095576 A1. Such a composition of an ophthalmic formulation does not only prevent precipitation of the Pritelivir hemihydrate at pH=4.0 (see Example 7) but also at pH 6.0 to 7.0 (see Example 8) which is required for formulations used on and at the eye. Moreover, it was found that not any commercially available artificial tears solution could be used. It is essential that the artificial tears solution or commercially available artificial tears solution contains glycerin, hypromellose, and polyethylene glycol 400. Preferably further ingredients could be present in the artificial tears solution. Such ingredients are at least one, preferably five, more preferably ten, and still more preferably fifteen compounds of the group consisting of carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, sodium borate, sodium chloride, sodium citrate, and sodium lactate.

Concerning the Pritelivir agent it was surprisingly found that the Pritelivir hemihydrate could not be replaced by the Pritelivir mesylate or the Pritelivir maleate due to insolubility and precipitation problems.

These findings in regard to the Pritelivir agent and the ingredients of the artificial tears solution are not even suggested by the state of the art documents including WO 2018/095576 A1, so that the ophthalmic formulations as disclosed herein are not obvious and not suggested by the state of the art.

Thus, starting from the gel formulation disclosed in WO 2018/095576 A1 a person skilled in the art had to realize that from the list of known Pritelivir agents such as the free base, the hemihydrate, the mesylate, the sulfate, the maleate would have to select the Pritelivir hemihydrate. In addition, the pH value of the gel had to be adapted to a pH value between 6.0 and 7.0. Now the skilled person had to realize that polyethylene glycol 400 is important and that hydroxypropyl cellulose has to be replaced by hypromellose, and finally that glycerin has to be added to the ophthalmic formulation. Consequently, a skilled person would need to realize a plurality of non-obvious steps to derive at the ophthalmic formulations disclosed herein starting form WO 2018/095576 A1 as closest prior art.

A further aspect of the present application relates to a method for the preparation of the ophthalmic formulation, wherein the method comprises the following steps:

I) providing N-[5-(aminosulfonyl)-4-methyl-1,3-thiazol-2-yl]-N-methyl-2-[4-(2-pyridinyl)phenyl]acetamide hemihydrate, II) providing polyethylene glycol, III) providing artificial tears solution containing glycerin, hypromellose, and polyethylene glycol 400 and optionally povidone, IV) preparing a stock solution of N-[5-(aminosulfonyl)-4-methyl-1,3-thiazol-2-yl]-N-methyl-2-[4-(2-pyridinyl)phenyl]acetamide hemihydrate in polyethylene glycol, V) diluting the stock solution with artificial tears solution until the desired concentration is reached, VI) adjusting the pH value by addition of an aqueous solution of an acid to the desired pH value, and VII) performing a sterile filtration by means of a suitable sterile filter to obtain the ophthalmic formulation.

This method preferably comprises at least one step of adjusting the pH value to the desired pH value which is preferably in the range of from 5.5 to 6.5. The ophthalmic solution can be adjusted to the desired pH value before and after sterile filtration. However, all pH ranges disclosed herein would likewise be acceptable for preparing the ophthalmic formulation.

The ophthalmic formulation should be stored at a temperature in the range of from 2° C. to 8° C., but can without degradation also be stored at room temperature.

The N-[5-(aminosulfonyl)-4-methyl-1,3-thiazol-2-yl]-N-methyl-2-[4-(2-pyridinyl)phenyl]acetamide hemihydrate is used within this method in the amounts and concentrations as disclosed above.

The same is true for the other ingredients such as the polyethylene glycol and the artificial tears solution which are both used in an amount and concentration as disclosed above. In the method described herein the use of PEG 400 and Visine® Tears solution as artificial tears solution is preferred.

The formulation is sterilized by filtration through a sterile/aseptic filter to produce a formulation that is sterile. The sterile filtration may be performed at any convenient temperature such as room temperature. The sterile filtration is through a filter with a pore size of preferably 0.20 μm or less.

The sterile filter material includes, but not limited to, polyvinylidene fluoride (PVDF), polypropylene (PE), polyphenylene oxide, polytetrafluorethylene (PTFE), ethylene-tetrafluoroethylene copolymer, polysulfone, polyethersulphone (PES), polyacetate (PA)/Nylon, PA-LE/Nylon, polyethersulfone, cellulose acetate (CA) and regenerated cellulose (RC).

However, it was found that the step of the sterile filtration is crucial and could only be performed using a particular type of sterile filter, namely a RC filter.

Regenerated cellulose (RC) is a class of materials manufactured by the conversion of natural cellulose to a soluble cellulosic derivative and subsequent regeneration, typically forming either a fiber (via polymer spinning) or a film (via polymer casting). The RC sterile filter is a hydrophilic membrane filter. Said RC sterile filter has a thickness in a range of 10 to 500 μm, preferably 50 to 400 μm, more preferably 100 to 300 μm, most preferably 150 to 200 μm. The RC sterile filter has a flow rate more than 10 mL/min*cm$^2$, preferably more than 15 mL/min*cm$^2$ at 25° C. at 0.7 bar.

The RC sterile filter was purchased from CZT (Klaus Trott Chromatographie-Zubehör, Kriftel, Germany; Article No. 802527020).

The RC sterile filter has a pore size of 0.2 μm and was connected via Luer Lok. The speciation of said RC sterile filter is summarized below:

| CZT-802527020 | Specification | Result |
|---|---|---|
| Luer-lock | Enhanced Luer-Lock (ISO 594-1) | Pass |
| Bubble point | >250 kPa | 362 |
| Ext. dimensions | 31.9 ± 0.3 mm × 25.7 ± 0.3 mm (height) | |
| Water Flow Rate | >10 ml/min. cm$^2$ (at 25 °C 0.7 bar) | 19.2 |
| UV extractable | According conditions specified below. Absorbance at | Water |
| | 214 < 0.04 AU | 0.0170 |
| | 254 < 0.04 AU | 0.0040 |
| | 280 < 0.04 AU | 0.0020 |

Consequently, the present application relates to a method for the preparation of the ophthalmic formulation, wherein the method comprises the following steps:

I) providing N-[5-(aminosulfonyl)-4-methyl-1,3-thiazol-2-yl]-N-methyl-2-[4-(2-pyridinyl)phenyl]acetamide hemihydrate, II) providing polyethylene glycol, III) providing artificial tears solution containing glycerin, hypromellose, and polyethylene glycol 400 and optionally povidone, IV) preparing a stock solution of N-[5-(aminosulfonyl)-4-methyl-1,3-thiazol-2-yl]-N-methyl-2-[4-(2-pyridinyl)phenyl]acetamide hemihydrate in polyethylene glycol, V) diluting the stock solution with artificial tears solution until the desired concentration is reached, VI) adjusting the pH value by addition of an aqueous solution of an acid to the desired pH value, and VII) performing a sterile filtration by means of a RC sterile filter to obtain the ophthalmic formulation.

EXAMPLES

1. Abbreviation List

PA Polyacetate
LE Low extractable
PFTE Polytetrafluorethylene
PVDF Polyvinylidenefluoride
CM Cellulose acetate
RC Regenerated cellulose
PP Polypropylene
PES Polyethersulphone

2. Materials

| Description | Manufacturer | Art No. or PZN-No |
|---|---|---|
| 50.0 mL tubes | Greiner-bio-one | 227261 |
| Sterile 2.0 mL tubes | Eppendorf | 0030 120.094 |
| Sterile 5.0 mL tubes | Eppendorf | 0030 119.401 |
| 150 mL sterile Filter system 0.22 µm | Corning | Ref 431154 |
| 10 ml-syringe Plastipak Luer-Lock | VWR | SS 10LE1 |
| Syringe filter 25 mm (PA/Nylon) 0.2 µm | CZT | 802510020 |
| Syringe filter 25 mm (PA/Nylon) 0.45 µm | CZT | 802510045 |
| Syringe filter 25 mm (PA-LE/Nylon) 0.2 µm | CZT | 802512020 |
| Syringe filter 25 mm (PA-LE/Nylon) 0.45 µm | CZT | 802512045 |
| Syringe filter 25 mm (PTFE) 0.2 µm | CZT | 802520020 |
| Syringe filter 25 mm (PTFE) 0.45 µm | CZT | 802520045 |
| Syringe filter 25 mm (PVDF) 0.2 µm | CZT | 802530020 |
| Syringe filter 25 mm (PVDF) 0.45 µm | CZT | 802530045 |
| Syringe filter 25 mm (CM) 0.2 µm | CZT | 802526020 |
| Syringe filter 25 mm (CM) 0.45 µm | CZT | 802526045 |
| Syringe filter 25 mm (CA) 0.2 µm | CZT | 802525020 |
| Syringe filter 25 mm (CA) 0.45 µm | CZT | 802525045 |
| Syringe filter 25 mm (RC) 0.2 µm | CZT | 802527020 |
| Syringe filter 25 mm (RC) 0.45 µm | CZT | 802527045 |
| Syringe filter 25 mm (PP) 0.2 µm | CZT | 802516020 |
| Syringe filter 25 mm (PP) 0.45 µm | CZT | 802516045 |
| Syringe filter 25 mm (PES) 0.2 µm | CZT | 802540020 |
| Syringe filter 25 mm (PES) 0.45 µm | CZT | 802540045 |

3. Equipment

| Equipment | Supplier |
|---|---|
| Climate chamber | Weißtechnik |
| PH meter 766 Calimatic | Knick |
| electrode SE104N | Knick |

4. Analytical Equipment

| Equipment | Name (Identifier) | Supplier |
|---|---|---|
| Autosampler | HTS PAL | CTC Analytics |
| Binary pump | 1200 Series | Agilent Technologies |
| Column oven | | |
| Degasser | | |
| Diode array detector (DAD) | | |

5. Preparation Protocol HPLC Analysis 5.1 Quantification 5.1.1 Preparation of the Eluents Add 10 mL HAc to 990 mL water and mix it Add 495 mL Methanol to 495 mL ACN and 10 mL HAc and mix it 5.2 Sample Preparation Ophthalmic Formulation Con=0.05 mg AIC090093/mL Related Impurities Dilute 500 µL of each sample with 500 µL ACN/MeOH/$H_2O$ ratio 25:25:50+1% HAc (1:2)

Mix it 5 s by vortexing

Final Concentration

Dilute 250 µL of each sample with 730 µL ACN/MeOH/$H_2O$ ratio 25:25:50+1% HAc and add 20 µL ACN/DMSO 4:1 (1:4)

Mix it 5 s by vortexing 5.3 Calibration Stock Solution 10 mg/Ml AIC090093

Weigh AIC090093 and solve in 10 mL DMSO

Mix it 15 min in the Vortex

| | Target weight |
|---|---|
| AIC090093 | 100.0 mg |
| DMSO | 10 mL |

5.4 Vehicle Solution

Mix PEG 200 and GenTeal Tears

Mix it 15 min in the Vortex

| | Target volume |
|---|---|
| PEG | 0.75 mL |
| Visine Tears | 14.25 mL |

5.5 Calibration, Qualification and Assay Working Standard Solution Preparation

| | Concentration AIC090093 [mg/mL] | Volume diluent ACN/DMSO 4 + 1 [µl] | Calibration stock solution [µl] |
|---|---|---|---|
| Blank | 0 | 1000 | 0 |
| Kal1 | 0.120 | 988 | 12 |
| Kal2 | 0.250 | 975 | 25 |
| Kal3 | 0.500 | 950 | 50 |
| Kal4 | 0.750 | 925 | 75 |
| Kal5 | 1.000 | 900 | 100 |
| Kal6 | 2.000 | 850 | 200 |
| Kal7 | 2.500 | 750 | 250 |
| Kal8 | 3.500 | 650 | 350 |
| QAL1 | 0.280 | 872 | 28 |
| QAL2 | 1.500 | 850 | 150 |
| QAL3 | 3.000 | 700 | 300 |
| AWS | 0.200 | 980 | 20 |

5.6 Dilution for HPLC

Dilute 20 µl calibration or QC-solution with 730 µl ACN/MeOH/$H_2O$ ratio 25:25:50+1% HAc and add 250 µL of the corresponding vehicle solution (1:50)

| | Concentration [mg/ml] |
|---|---|
| Blank | 0 |
| K1 | 0.002 |
| K2 | 0.005 |
| K3 | 0.010 |
| K4 | 0.015 |
| K5 | 0.020 |
| K6 | 0.040 |
| K7 | 0.050 |
| K8 | 0.075 |
| QC1 | 0.0056 |
| QC2 | 0.030 |
| QC3 | 0.060 |
| AWS | 0.0040 |

5.7 Measuring HPLC-DAD
Method: AIC090093_V1
Column: Luna C18(2) 5 μm, 150×2 mm, Phenomenex #84
Column oven temperature 23° C.
Auto Sampler-temperature. 5° C.
(CTC PAL)
PAL Sampler
Injection Volume: 10 μl
Overlap Injection Mode: No Overlap
Module Display Name: PAL
Module Type: PAL Sampler
Order: 1
PAL Method Information
Parameters of PAL Cycle
Air Volume (μl): 0
Pre Clean with Solvent 1 ( ): 0
Pre Clean with Solvent 2 ( ): 0
Pre Clean with Sample ( ): 0
Filling Speed (μl/s): 10
Filling Strokes ( ): 1
Inject to: LC VIv1
Injection Speed (μl/s): 5
Pre Inject Delay (ms): 500
Post Inject Delay (ms): 500
Post Clean with Solvent 1 ( ): 2
Post Clean with Solvent 2 ( ): 2
Valve Clean with Solvent 1 ( ): 1
Valve Clean with Solvent 2 ( ): 1
DAD Method
Peakwidth: >0.1 min (2 s response time) (2.5 Hz)
Slit: 4 nm
UV Lamp Required: Yes
Vis Lamp Required: Yes
Module Display Name: DAD
Module Type: G1315C
Order: 1
Analog Output 1
Analog 1 Zero Offset: 5%
Analog 1 Attenuation: 1000 mAU
Analog Output 2
Analog 2 Zero Offset: 5%
Analog 2 Attenuation: 1000 mAU Signals Signal table

| Row ID | Acquire | Signal | Wavelength (nm) | Bandwidth (nm) |
|---|---|---|---|---|
| 1 | No | Signal A | | |
| 2 | Yes | Signal B | 290 | 20 |
| 3 | No | Signal C | | |
| 4 | No | Signal D | | |
| 5 | No | Signal E | | |
| 6 | No | Signal F | | |
| 7 | No | Signal G | | |
| 8 | No | Signal H | | |

| Row ID | Use Ref. | Ref Wavel. (nm) | Ref Bandw. (nm) |
|---|---|---|---|
| 1 | | | |
| 2 | Yes | 450 | 50 |
| 3 | | | |
| 4 | | | |
| 5 | | | |
| 6 | | | |
| 7 | | | |
| 8 | | | |

Prepare Mode
Margin for negative Absorbance: 100 mAU
Autobalance
Autobalance Prerun: Yes
Autobalance Postrun: Yes
Spectrum
Spectrum Store: None
Stoptime
Stoptime Mode: As pump/injector
Posttime
Posttime Mode: Off
Column Comp. Method
Module Display Name: Column Comp.
Module Type: G1316B
Order: 1
Left Temperature Control
Temperature Control Mode: Temperature Set
Temperature: 23.0° C.
Enable Analysis Left Temperature
Enable Analysis Left Temperature On: Yes
Enable Analysis Left Temperature Value: 1.0° C.
Right Temperature Control
Right temperature Control Mode: Combined
Enable Analysis Right Temperature
Enable Analysis Right Temperature On: Yes
Enable Analysis Right Temperature Value: 1.0° C.
Stop Time
Stoptime Mode: As pump/injector
Post Time
Posttime Mode: Off
Binary Pump Method
Flow: 0.350 mL/min
Use Solvent Types: Yes
Low Pressure Limit: 0.00 bar
High Pressure Limit: 400.00 bar
Maximum Flow Gradient: 100.000 mL/min$^2$
Module Display Name: Binary Pump Module Type: G1312B
Order: 1

| Solvent Composition | | | | |
|---|---|---|---|---|
| Row ID | Channel | Solvent 1 | Name 1 | Used |
| 1 | A | $H_2O$ | 1% HAc | Yes |
| 2 | B | MeOH | ACN MeOH 1:1 1% HAc | Yes |
| Row ID | Percent (%) | | | |
| 1 | 98.0 | | | |
| 2 | 2.0 | | | |

| Timetable | | | | | |
|---|---|---|---|---|---|
| Row ID | Time (min) | A (%) | B (%) | Flow (mL/min) | |
| 1 | 2.00 | 98.0 | 2.0 | 0.350 | |
| 2 | 20.00 | 30.0 | 70.0 | 0.350 | |
| 3 | 20.10 | 2.0 | 98.0 | 0.350 | |
| 4 | 25.00 | 98.0 | 2.0 | 0.350 | |
| Row ID | Pressure (bar) | Contact A | Contact B | Contact C | Contact D |
| 1 | 400.00 | open | open | open | open |
| 2 | 400.00 | open | open | open | open |
| 3 | 400.00 | open | open | open | open |
| 4 | 400.00 | open | open | open | open |

Stroke A
Automatic Stroke Calculation A: Yes
Stroke B
Automatic Stroke Calculation B: Yes
Stop Time
Stoptime Mode: Time set
Stoptime: 25.00 min
Post Time
Posttime Mode: Off
External Contacts
Contact A: Open
Contact B: Open
Contact C: Open
Contact D: Open
Method Properties
Instrument Technique: Liquid Chromatography

6. Preparation of the Ophthalmic Formulation

Chemicals and Materials:

Pritelivir free base hemihydrate was synthesized by Carbogen amics.

Pritelivir maleate was synthesized by Carbogen amics.

Pritelivir mesylate monohydrate was synthesized by Carbogen amics.

Polyethylenglycol 200 (Polygylcol 200) was obtained from Clariant.

Polyethylenglycol 400 (Kollisolv 400) was purchased from BASF.

GenTeal® Tears solution was obtained from Alcon.

Thera® Tears solution was obtained from Akron Consumer Health.

Visine® Tears solution was obtained from Johnson & Johnson Healthcare.

Preparation Experiments

The following experiments describe the preparation of several different ophthalmic formulations with different drug substances (DS). The term Pritelivir hemihydrate as used herein refers to Pritelivir free base hemihydrate and to N-[5-(amino-sulfonyl)-4-methyl-1,3-thiazol-2-yl]-N-methyl-2-[4-(2-pyridinyl)phenyl]acetamide hemihydrate. The term Pritelivir maleate as used herein refers to to N-[5-(amino-sulfonyl)-4-methyl-1,3-thiazol-2-yl]-N-methyl-2-[4-(2-pyridinyl)phenyl]acetamide maleate and the term Pritelivir mesylate monohydrate as used herein refers to N-[5-(amino-sulfonyl)-4-methyl-1,3-thiazol-2-yl]-N-methyl-2-[4-(2-pyridinyl)phenyl]acetamide mesylate monohydrate.

Example 1

In order to prepare the new ophthalmic formulation the drug substance concentrations of both i) stock solution and ii) drug product which is administered to the patient need to be determined. For that purpose, a stock solution with different concentrations of Pritelivir free base hemihydrate in PEG 200 was diluted in GenTeal® tears and the precipitation was checked over time.

| Experiment | DS | Excipients | Scope |
|---|---|---|---|
| 1 | Pritelivir hemihydrate | PEG200 GenTeal ® Tears | Preparation of stock solution with different concentrations of DS. Dilution in GenTeal ® Tears with different final concentrations of the ophthalmic formulation. Check for precipitation over time in a pre-test. |

Preparation of Stock Solutions

All liquids and the DS were equilibrated to ≥20° C. Seven 10 mL tubes were provided. In each of these tubes, 5 ml of PEG 200 were added and the required amount of DS was dissolved therein to provide the following stock solutions: 30 mg/mL, 25 mg/mL, 20 mg/mL, 10 mg/mL, 5 mg/mL, 1 mg/mL, 0.05 mg/mL. The solutions were mixed by vortexing the tubes for 5 s and the tubes were shaken until the DS was dissolved.

Preparation Ophthalmic Formulations

The stock solutions were diluted with GenTeal® tears and the pH value was measured. After that the samples were checked for precipitation by visual inspection.

An ophthalmic formulation with a drug load of 24 mg/mL was obtainable without any visually detectable precipitation.

Example 2

To study the in-use stability over 5 weeks at room temperature (RT) and at a temperature in the range of from 2° C.-8° C., stock solutions with a concentration of 1.0 mg/mL of DS were prepared in PEG200 and in PEG400. The different stock solutions were diluted in 3 different compositions of artificial tears to a final concentration of 0.05 mg DS per mL ophthalmic formulation.

| Experiment | DS | Excipients | Scope |
|---|---|---|---|
| 2 | Pritelivir hemihydrate | PEG200 PEG400 GenTeal ® Tears Thera ® Tears | A stock solution in PEG with a concentration 1.0 mg/mL of DS was prepared by using two different grades of PEG (PEG200 and PEG400). |

-continued

| Experiment | DS | Excipients | Scope |
|---|---|---|---|
| | | Visine ® Tears | The different stock solutions were diluted in 3 different brands of artificial tears (0.05 mg/mL DS). |

Preparation of Stock Solution 1 mg/mL

All liquids and the DS were equilibrated to ≥20° C. Amounts of 10 ml of the respective PEG (either PEG 200 or PEG 400) were added to a 50 mL tube and 10 mg of DS were dissolved in each tube. The solutions were mixed by vortexing the tubes for 5 s and the tubes were shaken until the DS was dissolved.

Preparation Ophthalmic Formulations 0.05 mg/mL

An amount of 1.5 mL stock solution was diluted with 28.5 mL of the respective artificial tears solution (either GenTeal® Tears or Thera® Tears or Visine® tears) in a beaker and stirred for 2 min with a magnet stirrer. The pH value was determined and samples were taken before and after sterile filtration. The solutions were filtered through CA (cellulose acetate) 0.22 μm filter system. The content of the beaker was withdrawn and respectively 14 mL of the prepared formulation were added to two empty 50 mL tubes. In addition, one empty 2 mL tube was provided and 1.5 mL of the prepared formulation was added to the 2 mL tube. The samples were stored at RT and at a temperature in the range of from 2-8° C. over 5 weeks.

It was observed that the pH value of the ophthalmic formulation depended on the artificial tears solution used. The pH value of the artificial tears solution varied between 7.5 and 8.5.

However, it was quite surprising to note that after the sterile filtration of the ophthalmic formulation no DS could be detected by HPLC for all prepared formulations anymore.

Example 3

To study the filter compatibility a stock solution in PEG200 at a concentration 1.0 mg Pritelivir free base hemihydrate per mL of stock solution was diluted in GenTeal® tears to a concentration of 0.05 mg Pritelivir free base hemihydrate per ophthalmic formulation.

The ophthalmic formulation was filtered with different filter materials and pore sizes.

| Experiment | DS | Excipients | Scope |
|---|---|---|---|
| 3 | Pritelivir hemihydrate | PEG200 GenTeal ® Tears | A stock solution in PEG200 with a concentration 1.0 mg/mL of DS was diluted in GenTeal ® tears (0.05 mg/mL DS). The final solution was filtered with different filter materials and pore sizes. |

Preparation of Stock Solution 1 mg/mL DS

All liquids and the DS were equilibrated to ≥20° C. An amount of 10 ml of PEG 200 was added to a 50 mL tube and 10 mg of DS were dissolved therein. The solution was mixed by vortexing the tube for 5 s and the tube was shaken until the DS was dissolved.

Preparation of an Ophthalmic Formulation 0.05 mg/mL DS

The amount of 4.0 mL stock solution was diluted with 76.0 mL of GenTeal® tears and the solution was mixed by vortexing for 5 s stirring for 2 min until the DS was dissolved.

Filter Testing for all Syringe Filters (e.g. PA 0.2 μm)

The testing was repeated one time to have samples in duplicate (n=2). An amount of 6 mL of the ophthalmic formulation was withdrawn with a 10 mL syringe. An amount of 1 mL was used to determine the final concentration before filtration. The syringe was connected with a PA 0.2 μm filter via Luer Lok and the solution was filtered. Another sample was taken to determine the final concentration after filtration.

The filter was then disconnected from the syringe and an amount of 3 mL DMSO was withdrawn with the used 10 mL syringe. Then, the syringe was shaken smoothly. An amount of 1 mL was used to determine the final concentration after rinsing. The syringe was again connected to the used PA 0.2 μm filter via Luer Lok the DMSO was filtered. A sample was taken to determine the final concentration after washing.

This protocol was repeated for all tested filters: PA/Nylon, PALE/Nylon, PTFE, PVDF, CM, CA, RC, PP, PES. Each filter contained a filter material with a pore size of 0.2 μm and of 0.45 μm.

Surprisingly, only two filters were identified to be suitable for a sterile filtration of the ophthalmic formulation. The assay data before and after filtration of the filter materials PFTE 0.2 μm and RC 0.2 μm showed identical values.

Example 4

To study the feasibility of the sterile filtration with two grades of PEG and 3 different compositions of artificial tears, the experiment of Example 3 was repeated and, in addition the same conditions of the experiment of Example 3 were tested using a stock solution in PEG400 at a concentration 1.0 mg Pritelivir free base hemihydrate per mL stock solution and 2 other compositions of commercial available artificial tears.

| Experiment | DS | Excipients | Scope |
|---|---|---|---|
| 4 | Pritelivir hemihydrate | PEG200 PEG400 GenTeal ® Tears Thera ® Tears Visine ® Tears | The experiments 3 were repeated for confirmation. In addition the tests were repeated by using a stock solution in PEG400 with a concentration 1.0 mg/mL of DS and 2 other brands of commercially available artificial tears solutions. |

Preparation of PEG200 Stock Solution 1 mg/mL DS

All liquids and the DS were equilibrated to ≥20° C. An amount of 10 ml of PEG 200 was added to a 50 mL tube and 10 mg of DS were dissolved therein. The solution was mixed by vortexing the tube for 5 s and the tube was shaken until the DS was dissolved.

Preparation of PEG400 Stock Solution 1 mg/mL DS

All liquids and the DS were equilibrated to ≥20° C. An amount of 10 ml of PEG 400 was added to a 50 mL tube and 10 mg of DS were dissolved therein. The solution was mixed by vortexing the tube for 5 s and the tube was shaken until the DS was dissolved.

Preparation Ophthalmic Formulations 0.05 mg/mL DS

An amount of 2.0 mL of the respective stock solution was diluted with 38.0 mL of the respective artificial tears solution (either GenTeal® Tears, or Thera® Tears, or Visine® Tears) and the solution was mixed by vortexing for 5 s or by stirring for 2 min.

Filter Testing for all Syringe Filters

The testing was repeated to have samples in triplicate (n=3). An amount of 6 mL of the ophthalmic formulation was withdrawn with a 10 mL syringe. An amount of 1 mL was used to determine the final concentration before filtration. The syringe was connected with the filter via Luer Lok and the solution was filtered. Another sample was taken to determine the final concentration after filtration.

The filter was disconnected from the syringe and an amount of 2 mL DMSO was withdrawn with a fresh 10 mL syringe. The syringe was again connected to the used filter via Luer Lok and the DMSO was filtered. A sample was taken to determine the final concentration after washing.

This protocol was repeated for all tested filters. The following filter materials were tested: PTFE, PVDF, and RC each having a pore size of 0.2 μm.

The stock solution with PEG400 diluted with Thera® Tears showed identical results before and after filtration with the filter material PVDF 0.2 μm (syringe filter). For all other formulations the PVDF filter was not suitable. The PVDF filter was only suitable for one of 6 formulations.

The PFTE filter was suitable for all formulations diluted with GenTeal® and Visine® Tears.

The RC filter was suitable for all formulations containing any artificial tears solution and for PEG200 as well as for PEG400 stock solution.

Example 5

To study the in-use stability with two grades of PEG and 3 different compositions of artificial tears over 5 weeks at room temperature (RT) and 2° C.-8° C. in combination with the use of an RC filter material for sterile filtration, a stock solution in PEG with a concentration of 1.0 mg/mL of Pritelivir free base hemihydrate was prepared using either PEG200 or PEG400. The stock solutions were diluted in 3 different compositions of artificial tears at a concentration of 0.05 mg/mL and filtered through a suitable sterile filter.

| Experiment | DS | Excipients | Scope |
|---|---|---|---|
| 5 | Pritelivir hemihydrate | PEG200 PEG400 GenTeal ® Tears Thera ® Tears Visine ® Tears | A stock solution in PEG with a concentration 1.0 mg/mL of DS was prepared by using two different grades of PEG (PEG200 and PEG400). The different stock solutions were diluted in 3 different brands of artificial tears solutions (0.05 mg/mL DS) and filtrated through a suitable sterile filter. |

Preparation of PEG200 Stock Solution 1 mg/mL DS

All liquids and the DS were equilibrated to ≥20° C. An amount of 20 ml of PEG 200 was added to a 50 mL tube and 20 mg of DS were dissolved therein. The solution was mixed by vortexing the tube for 5 s and the tube was shaken until the DS was dissolved.

Preparation of PEG400 Stock Solution 1 mg/mL DS

All liquids and the DS were equilibrated to ≥20° C. An amount of 20 ml of PEG 400 was added to a 50 mL tube and 20 mg of DS were dissolved therein. The solution was mixed by vortexing the tube for 5 s and the tube was shaken until the DS was dissolved.

Preparation of Ophthalmic Formulations 0.05 mg/mL

The respective stock solutions were diluted with artificial tears solution in a beaker.

| Artifical Tears solution | Volume stock solution [mL] | Volume artifical tears [mL] |
|---|---|---|
| GenTeal ® Tears | 8.00 | 152.00 |
| Thera ® Tears | 2.50 | 47.50 |
| Visine ® Tears | 8.00 | 152.00 |

A sample was taken from each beaker on the top, in the middle and on the bottom to determine the final concentration.

Sterile Filtration

An amount of 50 mL of the ophthalmic formulation was withdrawn with a 50 mL syringe. The syringe was then connected to the respective filter via Luer Lok and the solution was filtered into a beaker. This step was repeated as often as needed by using the same filter and the same syringe for the corresponding batch number and the solution was then refilled into the same beaker. A sample was taken to determine the final concentration after filtration. Three empty 50 mL tubes and one 5 mL tube were provided and the content of one beaker was withdrawn. Amounts of 15 mL of the prepared formulation were added to each of the three empty 50 mL tube and 5 mL to the empty 5 mL tube. The samples were stored at room temperature and at a temperature in the range of rom 2° C.-8° C. over 5 weeks.

Only the ophthalmic formulation prepared by using a 1 mg/mL stock solution with PEG200 and diluted with GenTeal® Tears could be evaluated. In all other formulations precipitation occurred which probably started before the filtration step using a PTFE and RC filter each having a pore size of 0.2 μm.

Example 6

To further investigate the stability of the ophthalmic formulation, Pritelivir free base hemihydrate was provided as a 1 mg/mL stock solution in PEG400 and diluted with GenTeal® Tears.

| Experiment | DS | Excipients | Scope |
|---|---|---|---|
| 6 | Pritelivir hemihydrate | PEG400 GenTeal ® Tears | The results of experiment 5 were not satisfying so that stability of the ophthalmic formulation was further investigated. |

Preparation of 1 mg/mL Stock Solution PEG400

All liquids and the DS were equilibrated to ≥20° C. An amount of 20 ml of PEG 400 was added to a 50 mL tube and 20 mg of DS were dissolved therein. The solution was mixed by vortexing the tube for 5 s and the tube was shaken until the DS was dissolved.

Preparation Ophthalmic Formulations 0.05 mg/mL

All samples were prepared six fold. Ophthalmic formulations were prepared from the 1 mg/mL Pritelivir free base hemihydrate stock solution in PEG400 and GenTeal® Tears in a beaker:

| Artifical Tears | Volume stock solution [mL] | Volume artifical tears [mL] |
|---|---|---|
| GenTeal ® Tears | 0.5 | 9.5 |

A sample was taken from each beaker on the top, in the middle and on the bottom to determine the final concentration.

Sterile Filtration

The ophthalmic formulation was withdrawn with a 20 mL syringe. Then the syringe was connected to an RC 0.2 μm filter via Luer Lok and the solution was filtered into a tube. A sample was taken to determine the final concentration after filtration and the samples were stored at room temperature and at a temperature in the range of from 2° C.-8° C. over 5 weeks.

Six samples in total were prepared in sequence. It took about 5 minutes per sample. All formulations showed comparable assay content before and after filtration. Thus, the preparation time is a critical process parameter. After 1 week the samples stored at room temperature showed an increase of impurities. Samples which were stored at a temperature in the range of from 2-8° C. were stable over 1 week.

Example 7

To study the impact of the pH value on the tendency of the ophthalmic formulation to degrade and precipitate 3 different compositions of artificial tears were adjusted to pH 4.0, 5.0 and 6.0. A stock solution of Pritelivir free base hemihydrate in PEG400 at a concentration of 1.0 mg/mL was prepared. The stock solutions were diluted in the pH adjusted artificial tears at a Pritelivir free base hemihydrate concentration of 0.05 mg/mL and filtered through a RC 0.2 μm sterile filter. It turned out to be preferable to carry out the dilution step for each sample one after the other to keep the time before the filtration step short.

| Experiment | DS | Excipients | Scope |
|---|---|---|---|
| 7 | Pritelivir hemihydrate | PEG400 GenTeal ® Tears Thera ® Tears Visine ® Tears 0.1M HCl | The 3 different brands of artificial tears were adjusted to pH 4.0, 5.0 and 6.0. A stock solution in PEG400 with a concentration 1.0 mg/mL of DS was prepared. The stock solutions were diluted in the pH adjusted artificial tears solution (0.05 mg/mL DS) and filtrated through a RC 0.2 μm sterile filter. |

Preparation of 1 mg/mL Stock Solution PEG400

All liquids and the DS were equilibrated to ≥20° C. An amount of 40 ml of PEG 400 was added to a 50 mL tube and 40 mg of DS were dissolved therein. The solution was mixed by vortexing the tube for 5 s and the tube was shaken until the DS was dissolved.

Preparation of pH Adjusted Artificial Tears Solution

The following pH values 4.0, 5.0 and 6.0 were adjusted by adding respective amounts of hydrochloric acid to the artificial tears solution.

Preparation Ophthalmic Formulations 0.05 mg/mL

All samples were prepared as triplicates. One sample was prepared after the other to keep the preparation time short and to minimize the risk of precipitation. The stock solution was diluted with pH adjusted artificial tears solution in a tube and gently mixed. A sample was taken to determine the final concentration. An amount of 20 mL of the tube was withdrawn with a 20 mL syringe. Then, the syringe was connected to the RC 0.2 mm filter via Luer Lok and the solution was filtered in two portions of 10 mL each into two 50 mL tube. Another sample was taken to determine the final concentration after filtration.

| Volume stock solution [mL] | Volume artifical tears [mL] |
|---|---|
| 1.0 | 19.0 |

The samples were stored at room temperature and at a temperature in the range of from 2° C.-8° C. over 4 weeks.

None of the formulations showed a significant change in the pH level over 4 weeks. A higher risk for precipitation was observed for formulations with a higher pH value. The most stable ophthalmic formulation was Visine® Tears adjusted to pH 4. The formulation was stable over 3 weeks stored at room temperature and at a temperature in the range of from 2° C.-8° C.

Example 8

To determine an acceptable pH value for ophthalmic use, a stock solution of Pritelivir free base hemihydrate in PEG400 was prepared at a concentration 1.0 mg/mL. The stock solution was diluted in Visine® Tears solution to a concentration of 0.05 mg/mL Pritelivir free base hemihydrate. The ophthalmic formulation was adjusted to pH 6.0, 6.5 and 7.0 and afterwards filtered through a RC 0.2 μm sterile filter.

| Experiment | DS | Excipients | Scope |
|---|---|---|---|
| 8 | Pritelivir hemihydrate | PEG400 Visine ® Tears 0.1M HCl | A stock solution in PEG400 with a concentration 1.0 mg/mL of DS was prepared. The stock solution was diluted in Visine ® Tears solution (0.05 mg/mL DS). The final ophthalmic formulation was adjusted to pH 6.0, 6.5 and 7.0 and afterwards filtrated through a RC 0.2 μm sterile filter. |

Preparation of 1 mg/mL Stock Solution PEG400

All liquids and the DS were equilibrated to ≥20° C. An amount of 20 ml of PEG 400 was added to a 50 mL tube and 20 mg of DS were dissolved therein. The solution was mixed by vortexing the tube for 5 s and the tube was shaken until the DS was dissolved.

Pre-Testing for pH Adjustment

The stock solution was diluted with Visine® tears in a 50 mL tube and the resulting solution was mixed gently.

| Volume stock solution [mL] | Volume artifical tears [mL] |
|---|---|
| 0.4 | 7.6 |

A suitable amount of hydrochloric acid was added to adjust pH values of 6.0, 6.5 and 7.0. The resulting solutions were mixed gently.

Preparation Ophthalmic Formulations 0.05 mg/mL

All samples were prepared six fold. One sample was prepared after the other to keep the preparation time short and to minimize the risk of precipitation. The stock solution was diluted with Visine® tears solution in a 50 mL tube and the resulting solution was mixed gently.

| Volume stock solution [mL] | Volume artifical tears [mL] |
|---|---|
| 0.4 | 7.6 |

The amount of hydrochloric acid was added as determined in the pre-testing to adjust the pH to 6.0 and a sample was taken to determine the final concentration before filtration. The entire content of one tube was withdrawn with a 20 mL syringe. Then the syringe was connected to the RC 0.2 μm filter via Luer Lok and the solution was filtered into a 50 mL tube. A sample was taken to determine the final concentration after filtration of each tube. In addition, samples with corresponding pH values of 6.5 and 7.0 were prepared. All samples were stored at room temperature and at a temperature in the range of from 2° C.-8° C. over 2 weeks.

A higher risk for precipitation was observed for formulations with a higher pH value. The lower the pH value, the better the stability over two weeks. No significant change of the pH value was observed for all samples over two weeks. The most stable ophthalmic formulation was the ophthalmic formulation adjusted to pH 6.0. The formulation was stable over 1 week stored at room temperature. The ophthalmic formulation adjusted to pH 6.5 was almost as stable as the ophthalmic formulation adjusted to pH 6.0. The ophthalmic formulation adjusted to pH 7.0 showed decreased stability after one week.

Comparative Example 1

To study whether Pritelivir free base hemihydrate can be replaced with Pritelivir mesylate, Experiment 8 was repeated with Pritelivir mesylate monohydrate as DS.

| Experiment | DS | Excipients | Scope |
|---|---|---|---|
| 9 | Pritelivir mesylate | PEG400 Visine ® Tears 0.1M HCl | Ophthalmic formulation was prepared by using Pritelivir mesylate monohydrate as drug substance (DS). |

The preparation protocol of Example 8 was followed also for the ophthalmic formulation containing Pritelivir mesylate monohydrate as drug substance.

However, it was surprisingly found that Pritelvir mesylate monohydrate was not soluble in PEG400 at a concentration of 1 mg/mL. Precipitation was observed and the assay level decreased significantly after filtration.

Comparative Example 2

To study whether Pritelivir free base hemihydrate can be replaced with Pritelivir maleate, Experiment 8 was repeated with Pritelivir maleate as DS.

| Experiment | DS | Excipients | Scope |
|---|---|---|---|
| 10 | Pritelivir maleate | PEG400 Visine ® Tears 0.1M HCl | Ophthalmic formulation was prepared by using Pritelivir maleate as drug substance (DS). |

However, it was surprisingly found that it was not possible to prepare a 1 mg/mL stock solution.

CONCLUSION

From the three tested drug substances only the Pritelivir hemihydrate was suitable for the preparation of an ophthalmic formulation. The above discussed experiments 1-10 suggest that the preferred ophthalmic formulation is obtained from a 1 mg/mL PEG 400 stock solution which was diluted with Visine® Tears solution (also named Visine® Tears) and adjusted to pH 6.0.

Examples of Ophthalmic Formulations

Formulation 1:
- Prepared according to Example 8
- Stock solution: 1 mg Pritelivir free base hemihydrate in 1 ml PEG 400.
- Ophthalmic formulation:
- 0.4 ml stock solution and 7.6 ml Visine® Tears solution to obtain 8.0 ml ophthalmic formulation. pH was adjusted to 6.0.

Formulation 2:
- Prepared according to Example 8.
- Stock solution: 1 mg Pritelivir free base hemihydrate in 1 ml PEG 400.
- Ophthalmic formulation:
- 0.4 ml stock solution and 7.6 ml Visine® Tears solution to obtain 8.0 ml ophthalmic formulation. pH was adjusted to 6.5.

Formulation 3:
- Prepared according to Example 8.
- Stock solution: 1 mg Pritelivir free base hemihydrate in 1 ml PEG 400.
- Ophthalmic formulation:
- 0.4 ml stock solution and 7.6 ml Visine® Tears solution to obtain 8.0 ml ophthalmic formulation. pH was adjusted to 7.0.

Formulation 4:
- Prepared in line with Example 5.
- Stock solution: 1 mg Pritelivir free base hemihydrate in 1 ml PEG 200.
- Ophthalmic formulation:
- 8 ml stock solution and 152 ml GenTeal® Tears solution to obtain 160.0 ml ophthalmic formulation. In addition, the pH was adjusted to 6.0.

Formulation 5:
- Prepared in line with Example 5.
- Stock solution: 1 mg Pritelivir free base hemihydrate in 1 ml PEG 200.
- Ophthalmic formulation:
- 2.5 ml stock solution and 47.5 ml GenTeal® Tears solution to obtain 50.0 ml ophthalmic formulation. In addition, the pH was adjusted to 6.8.

Formulation 6:
- Prepared in line with Example 4.
- Stock solution: 1 mg Pritelivir free base hemihydrate in 0.5 ml PEG 200 and 0.5 ml PEG400.
- Ophthalmic formulation:
- 8 ml stock solution and 152 ml Thera® Tears solution to obtain 160.0 ml ophthalmic formulation. In addition, the pH was adjusted to 7.0.

Formulation 7:
- Stock solution: 1.5 mg Pritelivir free base hemihydrate in 1 ml PEG 300.
- Artificial tears solution: 2.5 g/L glycerin, 2 g/L hypromellose, and 11.28 g/L polyethylene glycol 400 in purified water containing polyvinyl alcohol, povidone, propylene glycol, ascorbic acid, magnesium chloride, potassium chloride, sodium borate, sodium chloride, sodium citrate, and/or sodium lactate.

Ophthalmic formulation:

1 ml stock solution and 15 ml artificial tears solution to obtain 16.0 ml ophthalmic formulation. pH was adjusted to 6.5.

The invention claimed is:

1. An ophthalmic formulation comprising:

a) N-[5-(aminosulfonyl)-4-methyl-1,3-thiazol-2-yl]-N-methyl-2-[4-(2-pyridinyl)phenyl]acetamide hemihydrate, b) polyethylene glycol, and c) artificial tears solution, wherein the artificial tears solution contains glycerin, hypromellose, water as solvent, and polyethylene glycol 400 and optionally povidone, and wherein the ophthalmic formulation has a pH value in a range of 4.0 to 6.5, and wherein the artificial tears solution is contained in the ophthalmic formulation in an amount in the range of from 0.9 g per ml ophthalmic formulation to 1.3 g per ml ophthalmic formulation.

2. The ophthalmic formulation according to claim 1, wherein the ophthalmic formulation has a viscosity between 25 cps and 50 cps.

3. The ophthalmic formulation according to claim 1, wherein the polyethylene glycol has an average molecular weight in the range of from 200 g/mol to 400 g/mol.

4. The ophthalmic formulation according to claim 1, wherein the polyethylene glycol is contained in the ophthalmic formulation in an amount in the range of from 40 μg per ml ophthalmic formulation to 70 μg per ml ophthalmic formulation.

5. The ophthalmic formulation according to claim 1, wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount in the range of from 40 μg per ml ophthalmic formulation to 60 μg per ml ophthalmic formulation.

6. The ophthalmic formulation according to claim 1, wherein the artificial tears solution further contains carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, purified water, sodium borate, sodium chloride, sodium citrate, and/or sodium lactate.

7. The ophthalmic formulation according to claim 1, wherein the artificial tears solution contains 0.2% by weight glycerin, 0.2% by weight hypromellose, and 1% by weight PEG 400.

8. A method for the production of the ophthalmic formulation as defined in claim 1, the method comprising the steps I) providing N-[5-(aminosulfonyl)-4-methyl-1,3-thiazol-2-yl]-N-methyl-2-[4-(2-pyridinyl)phenyl]acetamide hemihydrate, II) providing polyethylene glycol, III) providing artificial tears solution, wherein the artificial tears solution contains glycerin, hypromellose, water as solvent, and polyethylene glycol 400 and optionally povidone, IV) preparing a stock solution of N-[5-(aminosulfonyl)-4-methyl-1,3-thiazol-2-yl]-N-methyl-2-[4-(2-pyridinyl)phenyl]acetamide hemihydrate in polyethylene glycol, V) diluting the stock solution with artificial tears solution, VI) adjusting the pH value by addition of an aqueous solution of an acid to a pH value in a range of 4.0 to 6.5, and VII) performing a sterile filtration by means of a suitable sterile filter to obtain the ophthalmic formulation, wherein the artificial tears solution is contained in the ophthalmic formulation in an amount in the range of from 0.9 g per ml ophthalmic formulation to 1.3 g per ml ophthalmic formulation.

9. The method according to claim 8, wherein the sterile filtration is performed with a regenerated cellulose (RC) 0.2 μm filter.

10. The method according to claim 8, wherein the polyethylene glycol is polyethylene glycol 400 and/or the artificial tears solution contains 0.2% by weight glycerin, 0.2% by weight hypromellose, and 1% by weight PEG 400.

11. The ophthalmic formulation according to claim 1, wherein the polyethylene glycol is contained in the ophthalmic formulation in an amount in the range of from 40 μg per ml ophthalmic formulation to 70 μg per ml ophthalmic formulation, and wherein the N-[5-(aminosulfonyl)-4-methyl-1,3-thiazol-2-yl]-N-methyl-2-[4-(2-pyridinyl)-phenyl]acetamide hemihydrate is contained in the ophthalmic formulation in an amount in the range of from 40 μg per ml ophthalmic formulation to 60 μg per ml ophthalmic formulation.

12. The ophthalmic formulation according to claim 1, wherein the polyethylene glycol has an average molecular weight in the range of from 200 g/mol to 400 g/mol and the ophthalmic formulation has a viscosity between 25 cps and 50 cps.

13. The ophthalmic formulation according to claim 12, wherein the artificial tears solution further contains carboxymethylcellulose, dextran, polysorbate, polyvinyl alcohol, povidone, propylene glycol, ascorbic acid, benzalkonium chloride, boric acid, dextrose, disodium phosphate, glycine, magnesium chloride, potassium chloride, purified water, sodium borate, sodium chloride, sodium citrate, and/or sodium lactate.

14. The ophthalmic formulation according to claim 1, wherein the polyethylene glycol has an average molecular weight in the range of from 200 g/mol to 400 g/mol and is present in an amount from 20 μg per ml ophthalmic formulation to 100 μg per ml ophthalmic formulation.

15. The method according to claim 8, wherein the aqueous solution of an acid is an aqueous solution of hydrochloric acid or hydrobromic acid.

16. The method according to claim 8, wherein the artificial tears solution contains 0.2% by weight glycerin, 0.2% by weight hypromellose, and 1% by weight PEG 400.

17. A method of treating a herpes infection of the eye in a subject comprising administering to the subject one to five drops two or three times a day of the ophthalmic formulation according to claim 1.

* * * * *